United States Patent [19]

Gilbert et al.

[11] Patent Number: 5,017,688

[45] Date of Patent: May 21, 1991

[54] PEPTIDES INVOLVED IN THE PATHOGENESIS OF HIV INFECTION

[75] Inventors: Walter Gilbert, Cambridge; Richard A. Fisher, Brookline; Vicki L. Sato, Cambridge; Kuzhalmannam L. Ramachandran, Natick, all of Mass.

[73] Assignee: Biogen, Inc., Cambridge, Mass.

[21] Appl. No.: 430,898

[22] Filed: Oct. 30, 1989

Related U.S. Application Data

[63] Continuation of Ser. No. 41,936, Apr. 24, 1987, abandoned, which is a continuation-in-part of Ser. No. 873,621, Jun. 12, 1986, abandoned.

[51] Int. Cl.$^5$ ............... C07K 7/08; A61K 37/02; A61K 39/12
[52] U.S. Cl. ............... 530/326; 530/327; 424/88; 424/89; 514/13; 514/14
[58] Field of Search ............... 424/88, 89; 514/13, 514/14; 530/326, 327

[56] References Cited

U.S. PATENT DOCUMENTS

| | | | |
|---|---|---|---|
| 4,520,113 | 5/1985 | Gallo et al. | 436/504 |
| 4,591,552 | 5/1986 | Newrath | 530/324 |
| 4,629,783 | 12/1986 | Cosand | 530/325 |

FOREIGN PATENT DOCUMENTS

| | | |
|---|---|---|
| 181150 | 5/1986 | European Pat. Off. |
| 187041 | 7/1986 | European Pat. Off. |
| 199301 | 10/1986 | European Pat. Off. |
| 199438 | 10/1986 | European Pat. Off. |
| 201716 | 11/1986 | European Pat. Off. |
| 214709 | 3/1987 | European Pat. Off. |
| 279688 | 8/1988 | European Pat. Off. |
| 286264 | 10/1988 | European Pat. Off. |
| 86-01827 | 3/1986 | PCT Int'l Appl. |
| 8602383 | 4/1986 | PCT Int'l Appl. |

OTHER PUBLICATIONS

N. T. Chang et al., "An HTLV-III Peptide Produced by Recombinant DNA is Immunoreactive with Sera from Patients with AIDS", *Nature*, 315, pp. 151–54 (1985) [Chang et al. I].

N. T. Chang et al., "Expression in *Escherichia coli* of Open Reading Frame Gene Segments of HTLV-III", *Science*, 228, pp. 93–96 (1985) [Chang et al. II].

T. C. Chanh et al., "Induction of Anti-HIV Neutralizing Antibodies by Synthetic Peptides", *EMBO J.*, 5, pp. 3065–+71 (1986).

R. Crowl et al., "HTLV-III env Gene Products Synthesized in *E. coli* are Recognized by Antibodies Present in the Sera of AIDS Patients", *Cell*, 41, pp. 979–986 (Jul. 1986).

R. C. Kennedy et al., "Antiserum to a Synthetic Peptide Recognizes the HTLV-III Envelope Glycoprotein", *Science*, 231, pp. 1556–1559 (Mar. 28, 1986).

D. Pauletti et al., "Application of a Modified Computer Algorithm in Determining Potential Antigenic Determinants Associated with the AIDS Virus Glycoprotein", *Analytical Biochemistry*, 151, pp. 540–546.

L. Ratner et al., "Complete Nucleotide Sequence of the AIDS Virus, HTLV-III", *Nature*, 313, pp. 277–284 (Jan. 1985).

Fauci et al., Ann. Inst. Pasteur/Immunol. vol. 138, pp. 261–268 (1987).

Broder et al., The Lancet, pp. 627–630 (1985).

McClure et al., Current Topics in AIDS, vol. 1, Gottlieb et al. (Ed.) John Wiley & Sons, New York, pp. 95–117 (1987).

Fauci, Proc. Natl. Acad. Sci. USA vol. 83 pp. 9278–9283 (12/1986).

Chang et al., Bio/Technology vol. 3, pp. 905–909 (10/85).

Starcich et al., Cell, vol. 45 pp. 637–648, (6/6/86).

*Primary Examiner*—John Doll
*Assistant Examiner*—Christina Chan
*Attorney, Agent, or Firm*—James F. Haley, Jr.; Margaret A. Pierri; Doreen F. Shulman

[57] ABSTRACT

This invention relates to peptides involved in the pathogenesis of human immunodeficiency virus ("HIV"). More particularly, this invention relates to peptides from the env region of the HIV genome and the use of such peptides in methods and compositions for preventing, treating, or detecting acquired immune deficiency syndrome ("AIDS") infection.

1 Claim, 1 Drawing Sheet

FIGURE 1

AA 600-750 of HIV env :
GIWGCSGKLICTTAVPWNAS
WSNKSLEQIWNNMTWMEWDR
EINNYTSLIHSLIEESQNQQ
EKNEQELLELDKWASLWNWF
NITNWLWYIKLFIMIVGGLV
GLRIVFAVLSVVNRVRQGYS
PLSFQTHLPIPRGPDRPEGI
EEEGGERDRD Peptide 1 (AA 616-632 of HIV env) : PWNASWSNKSLEQIWNN Peptide 2 (AA 667-680 of HIV env) : LLELDKWASLWNWF Peptide 3: (AA 627-639 of HIV env) : EQIWNNMTWMEWD Peptide 4 (AA 728-751 of HIV env) : LPIPRGPDRPEGIEEEGGERDRDR Peptide 5 (AA 426-450 of HIV env) : RIKQIINMWQEVGKAMYAPPISGQI Peptide 6 (AA 496-519 of HIV env) : VKIEPLGVAPTKAKRRVVQREKRA Peptide 31 (AA 148-165 of HIV env) : NSSSGRMIMEKGEIKNCS Peptide 64 (AA 627-639 of HIV env) : EQIWNNMTWMEWD Peptide 78 (AA 298-314 of HIV env) : SVEINCTRPNNNTRKSI

PEPTIDES INVOLVED IN THE PATHOGENESIS OF HIV INFECTION

This is a continuation of application Ser. No. 041,936, filed Apr. 24, 1987, now abandoned, which is a continuation-in-part of application Ser. No. 873,621, filed June 12, 1986, now abandoned, both entitled "Peptides Involved In The Pathogenesis Of HIV Infection."

TECHNICAL FIELD OF INVENTION

This invention relates to peptides involved in the pathogenesis of human immunodeficiency virus ("HIV"). More particularly, this invention relates to peptides from the env region of the HIV genome and the use of such peptides in methods and compositions for preventing, treating, or detecting acquired immune deficiency syndrome ("AIDS") infection.

BACKGROUND ART

Acquired immune deficiency syndrome ("AIDS") is a disease characterized by severe or, typically, complete immunosuppression and attendant host susceptibility to a wide range of opportunistic infections and malignancies. AIDS' complete clinical manifestation is usually preceded by AIDS related complex ("ARCS"), a syndrome accompanied by symptoms such as lymphadenopathy, fever and weight loss.

The human immunodeficiency virus ("HIV") retrovirus is thought to be the etiological agent responsible for AIDS infection and the ARCS syndrome [M. G. Sarngadharan et al., "Detection, Isolation, and Continuous Production of Cytopathic Retroviruses (HTLV-III) From Patients With AIDS and Pre-AIDS", *Science*, 224, pp. 497-508 (1984)].* Between 85 and 100% of the AIDS/ARCS patient population test seropositive for HIV [G. N. Shaw et al., "Molecular Characterization of Human T-Cell Leukemia (Lyphotropic) Virus Type III In The Acquired Immune Deficiency Syndrome", Science, 226, pp. 1165-70 (1984)]. * In this application, human immunodeficiency virus ("HIV"), the generic term adopted by the human retrovirus subcommittee of the International Committee on Taxonomy of Viruses to refer to independent isolates from AIDS patients, including human T-cell lymphotropic virus type III ("HTLV-III"), lymphadenopathy-associated virus ("LAV") and AIDS-associated retrovirus ("ARV") will be used.

Upon infection of a host, the primary targets of the HIV virus are T-4 lymphocytes, also known as helper or inducer cells. T-4 lymphocytes interact with other specialized cell types of the immune system to confer immunity to or defense against infection. More specifically, T-4 lymphocytes stimulate production of growth factors which are critical to the functioning of the immune system. For example, they act to stimulate B cells, the descendants of hemopoietic stem cells, which promote the production of defensive antibodies. They also activate macrophages ("killer cells") to attack infected or otherwise abnormal host cells, and induce monocytes ("scavenger cells") to encompass and destroy invading microbes. Accordingly, when T-4 lymphocytes are rendered non-functional by HIV infection, this complex immune defense system is destroyed and the host becomes susceptible to a wide range of opportunistic infections. In addition to T-4 lymphocytes, the HIV virus has also been shown to infect central nervous system cells, macrophages and B lymphocytes [J. M. Ismach, "AIDS: Can The Nation Cope", *Medical World News* (Aug. 25, 1985)].

The genome of retroviruses such as HIV contains three regions encoding structural proteins. The gag region encodes the core proteins of the virion. The pol region encodes the virion RNA-dependent DNA polymerase (reverse transcriptase). The env region encodes the major glycoprotein found in the membrane envelope of the virus and in the cytoplasmic membrane of infected cells. The capacity of the virus to attach to target cell receptors and to cause fusion of cell membranes are two HIV virus properties controlled by the env gene. These properties are believed to play a fundamental role in the pathogenesis of the virus.

HIV env proteins arise from a precursor polypeptide that, in mature form, is cleaved into a large heavily glycosylated exterior membrane protein of about 481 amino acids—gp120—and a smaller transmembrane protein of about 345 amino acids which may be glycosylated—gp41 [L. Ratner et al., "Complete Nucleotide Sequence Of The Aids Virus, HTLV-III", Nature", 313, pp. 277-84 (1985)].

In the absence to date of effective treatments for AIDS, many efforts have centered on prevention of the disease. Such preventative measures include HIV antibody screening of all blood, organ and semen donors and education of AIDS high-risk groups regarding transmission of the disease.

Experimental or early-stage clinical treatment of AIDS and ARCS conditions have included the administration of antiviral drugs, such as HPA-23, phosphonoformate, suramin and ansamycin, which apparently interfere with replication of the virus by inhibiting its reverse transcriptase. Administration of some of these drugs in effective amounts has, however, been accompanied by undesirable and debilitating side effects. Other proposed methods for treating AIDS have focused the administration of alpha interferon or the application of hybridoma technology. Most of these treatment strategies are expected to require the co-administration of immunomodulators, such as interleukin-2. However, while some of these treatments are promising, none has been shown to be truly effective.

Recent studies have also demonstrated that HIV is experiencing genetic drift in humans. At least two classes of the virus have now been identified in AIDS patients in the United States. Furthermore, patients having high levels of HIV neutralizing antibodies suffer more serious forms of the disease than those patients with poor neutralizing capabilities [Dr. William Haseltine, speech at Memorial Sloan-Kettering Cancer Center, October 9, 1985]. These recent observations suggest serious obstacles to the development of an effective vaccine or monoclonal antibody-directed therapeutic method against HIV AIDS infections.

Accordingly, despite these developments to date, the need exists for the development of effective agents for the prevention, treatment and diagnosis of HIV and AIDS-related infections.

DISCLOSURE OF THE INVENTION

The present invention solves the problems referred to above by providing peptides involved in the pathogenesis of the HIV virus. According to one embodiment, the peptides of this invention are selected from the group consisting of peptides characterized by an amino acid sequence derived substantially from the region between about amino acid 600 and amino acid 750 of the HIV env gene. This region is believed to have an important role in virus-mediated pathogenic events. More preferably, the peptides of this invention consist substantially of the following amino acid sequences of the HIV env gene—peptide 1: amino acids 616-632; peptide 2: amino acids 667-680; peptide 3: amino acids 627-639*; peptide 4: amino acids 728-751 and peptide 64: amino acids 627-639. This invention also includes the D-retro form of each of the above-identified peptides—those produced by synthesis with D amino acids in the opposite orientation, beginning with the carboxy terminal amino acid of the L form. * Due to an inadvertent mislabelling of the peptide sample assayed, the 873,621 application referred to peptide 3 as amino acids 702-715 of the HIV env gene. Subsequent amino acid sequencing of the peptide sample demonstrated that the peptide labelled "peptide 3" in fact had the sequence: amino acids 627-639 of the HIV env gene. As employed in the present application, therefore, "peptide 3" refers to a peptide having the sequence of amino acids 627-639 of the HIV env gene. This is the same sequence as peptide 64. Thus, peptides 3 and 64 are identical. The two numbers are used to distinguish the preparations of the two peptides.

Other embodiments of this invention include peptide 5, which consists substantially of amino acids 426-450 of the HIV env gene, peptide 6, which consists substantially of amino acids 496-519 of the HIV env gene, peptide 31, which consists substantially of amino acids 148-165 of the HIV env gene and peptide 78, which consists substantially of peptides 298-314 of the HIV env gene. This invention also includes the D-retro form of each of the above-identified peptides. These peptides produce antisera which, in conventional assays, bind to the HIV virus, inhibit syncytium formation or neutralize the virus. In addition, the peptides themselves may be capable of inhibiting HIV-directed syncytium formation or neutralizing HIV in conventional assays. Such peptides, therefore, are useful in compositions and methods for preventing, treating and detecting AIDS infection.

The peptides of this invention comprise functional regions of the HIV env protein involved in virus-mediated events, such as adsorption to normal cells and syncytium formation, which contribute to the pathogenesis of the disease. The functional regions encompassed by these peptides also correspond to immunogenic determinants of the HIV env gene which are highly conserved. Accordingly, these peptides comprise segments of HIV env protein which are highly immunogenic and are involved in virus pathogenesis over the range of genetic variants of the HIV virus.

The peptides of this invention may be advantageously used in vaccines or therapeutic compositions which elicit antibodies reactive with the native env protein of the HIV virus or which interfere with the virus by neutralization or inhibition of syncytium formation. Furthermore, these peptides are easily modified in composition and conformation to improve the specific activity of those peptides against the HIV virus. In addition, these peptides may be used as diagnostic agents for detecting HIV infections.

BRIEF DESCRIPTION OF THE DRAWINGS

FIG. 1 depicts the amino acid sequences of each of peptides 1-6, 31, 64 and 78 of this invention, as well as that of the region between amino acid 600 and amino acid 750 of the HIV env gene. In this figure, the amino acids are represented by single letter codes as follows:

| Phe: F | Leu: L | Ile: I | Met: M |
|---|---|---|---|
| Val: V | Ser: S | Pro: P | Thr: T |
| Ala: A | Tyr: Y | His: H | Gln: Q |
| Asn: N | Lys: K | Asp: D | Glu: E |
| Cys: C | Trp: W | Arg: R | Gly: G |

DETAILED DESCRIPTION OF THE INVENTION

Referring now to FIG. 1, we prepared various peptides corresponding to segments of the env gene of the HIV genome and tested them in several conventional assays to demonstrate that they display activities reflecting their involvement in virus-mediated pathogenic events.

It should be understood that the present invention is not limited to the illustrative peptides depicted in FIG. 1. Instead, a peptide falling within the scope of this invention may extend outside of or comprise less than the region between amino acid 600 and amino acid 750 of the HIV env gene, as long as a substantial part of that peptide is characterized by an amino acid sequence from that region, or segments or combinations thereof, and that peptide demonstrates the desired immunological or biological activity against HIV. In addition, peptides according to this invention include those having amino acid sequences which are longer or shorter in length than those of peptides 1-4 and 64 or which comprise segments or combinations thereof, as long as such peptides consist substantially of the region between amino acids 600-750 of the HIV env gene and demonstrate the desired immunological or biological activity. Furthermore, peptides according to this invention include those characterized by a sequence of amino acids which is longer or shorter than that of any one of peptide 5, peptide 6, peptide 31 or peptide 78, or which comprise segments of each of those peptides and which display immunological or biological activity against HIV.

Accordingly, it should be understood that the specific selection of any one peptide within the peptides of this invention is not critical. Such a selection may be carried out by taking a number of peptides and testing them for their immunological and biological activity against HIV as described herein.

The peptides according to this invention may be prepared by conventional synthesis using any of the known peptide synthesis methods, including synthesis on a solid support. The peptides of the invention may also be prepared in appropriate hosts transformed with DNA sequences that code for the desired peptide. For example, a peptide of this invention may be prepared by the fermentation of appropriate hosts that have been transformed with and which express a DNA sequence encoding that peptide. Alternatively, DNA sequences coding for several of the peptides of this invention may be linked together and those sequences may then be used to transform appropriate hosts to permit the expression of peptides involved in the pathogenesis of HIV infection. A combination of such methods may also be employed. In a preferred embodiment of this invention, chemical synthesis alone is employed. By means of that method, the peptides of this invention are additionally advantaged because they are easily purified and are non-biological in origin.

The peptides of this invention are preferably coupled to one or more carrier proteins, such as keyhole limpet hemocyanin ("KLH") before use in the compositions and methods described herein. The peptides are coupled to the carrier protein in various conventional ways, such as those described by M. Reichlin, "Use Of Glutaraldehyde As A Coupling Agent For Proteins And Peptides", *Methods In Enzymology,* 70, pp. 159-65 (1980).

After preparing the peptide and coupling it to the carrier protein, if desired, the antigen is employed in the methods and compositions of this invention in a conventional manner. For example, the peptide or coupled peptide, alone or in combination nation with other peptides of this invention, is usually mixed with one or a combination of well-recognized adjuvants and additives, preferably by first dissolving the peptide, for example, in PBS with 0.1% SDS. In other embodiments of this invention, the peptides may be linked to hydrophobic groups to build the adjuvant into the composition. Of course, it should be understood that other well-known methods of preparing therapeutic compositions may be employed using the peptides of this invention.

The above-prepared compositions are then employed in a conventional manner for the treatment of HIV infections. Such methods of treatment and their dosage levels and requirements are well-recognized in the art and may be chosen by those of skill in the art from available methods and techniques. For example, the peptides of this invention may be combined with a pharmaceutically acceptable adjuvant for administration to an HIV-infected patient in a pharmaceutically acceptable manner and in an amount effective to lessen the severity of the HIV infection. The dosage and treatment regimens will depend upon factors such as the patient's health status, the severity and course of infection and the judgment of the treating physician.

Alternatively, the peptides of this invention are useful in vaccines and methods for protecting humans against HIV infection for at least some period of time. The peptides may be employed in these vaccines and methods either alone or together with other peptides of this invention in a manner consistent with the conventional utilization of antigens in vaccines. For example, the peptides of this invention may be combined with pharmaceutically acceptable adjuvants conventionally employed in vaccines and administered in immunologically effective amounts to protect patients for some time against HIV infection.

Both the compositions and vaccines of this invention may be administered to patients via conventional modes of administration. The frequency of administration will depend upon factors such as the particular composition or vaccine employed and the condition of the patient. The need for subsequent treatments with these compositions or boosters of these vaccines will depend upon the results of the initial treatment or vaccination.

In addition, the peptides of this invention and the antibodies raised to them may be employed in presently available methods and kits designed to detect the presence of HIV and antibodies to HIV in blood, organ or semen samples.

In order that the invention described herein may be more fully understood, the following examples are set forth. It should be understood that these examples are for illustrative purposes only and are not to be construed as limiting this invention in any manner.

EXAMPLE I

Preparation Of Peptides Involved In The Pathogenesis of HIV Infection

We synthesized peptides 1-6, 31, 64 and 78, corresponding to segments of the env gene of the HIV genome. These peptides are depicted in FIG. 1, in which the amino acid numbering corresponds to that set forth for the env gene in L. Ratner et al., "Complete Nucleotide Sequence Of The AIDS Virus, HTLV-III", *Nature,* 313, pp. 277-84(1985).

We synthesized the peptides using an improved version of the solid phase method described by R. B. Merrifield, "Solid Phase Peptide Synthesis. I. The Synthesis Of A Tetrapeptide", *J. Am. Chem. Soc.,* 83, pp. 2149-54 (1963), using an Applied Biosystems Model 430A peptide synthesizer and reagents and procedures as supplied by producer. In this improved method, we deblocked and cleaved the protected peptides from the resin with liquid HF containing 10% anisole, in a variation of the method described by S. Sakakibara et al., "Use Of Anhydrous Hydrogen Fluoride In Peptide Synthesis. I. Behavior of Various Protective Groups In Anhydrous Hydrogen Fluoride", *Bull. Chem. Soc. Jap.,* 40, pp. 2164-68 (1967).

We first purified the peptides cleaved from the resin by partition chromatography on a Sephadex LH20 column using n-Butanol/water (6/100) as eluent. The eluate was further purified by semipreparative high pressure reversed phase chromatography on an Altex Ultrasphere-ODS column, by elution with a 0.1% TFA acetonitril gradient. After we hydrolyzed the eluate with 6N HCl for 18 hours, we carried out amino acid analysis on a Beckman amino acid analyzer to confirm the amino acid sequences of the peptides produced.

Immunological Activity Of The Peptides Of This Invention

1. Coupling Of Peptides To Carrier Proteins

In one embodiment of this invention, peptides 1-6,* 31, 64 and 78 were preferably coupled to one or more carrier proteins before use. Accordingly, we coupled each of those peptides prepared as described above to the carrier protein keyhole limpet haemocyanin (KLH, Sigma) by mixing 2 mg of peptide in 2 ml sodium phosphate buffer (0.1M, pH=8) with 5 mg of KLH in 2 ml sodium phosphate buffer (0.1 M, pH=8). We then added 1 ml of a 0.25% glutaraldehyde solution to the mixture in several portions over a period of 1 hour. We stirred the resulting mixture for another 6 hours and then dialyzed it against PBS overnight. *Due to an inadvertent error, the 873,621 application stated that peptides 2 and 3 were used in non-coupled form. Peptides 2 and 3 as employed in the examples of both the '621 application and the present application were used in coupled form.

For use in vaccine compositions, the peptides of this invention may be coupled with tetanus toxoid antigen, diphtheria toxoid antigen or another natural or synthetic carrier suitable for use in humans using conventional techniques. Alternatively, the peptides may be coupled with a suitable adjuvant to enhance the immune response in the patient. The peptides may also be used in combination with any suitable synthetic low molecular weight carrier before use. Finally, an additional cysteine residue may be added to the C or N terminus of the peptide for coupling to a suitable carrier by disulfide linkage.

2. Inoculation Of Test Animals

We emulsified each of the KLH-coupled peptides 1-6, 31, 64 and 78 with Freund's complete adjuvant in a 1:1 ratio. Subsequently, we inoculated groups of 3 BALB/CJ mice (Jackson Laboratory, Bar Harbor, Maine) by subcutaneous injection of 100 μg/250 μl of the emulsification into each mouse. On following days 14 and 35, each mouse received a booster injection of 100 μg/250 μl of the same coupled peptide emulsified 1:1 in Freund's incomplete adjuvant. Tail bleeds were taken on days 21 and 42, with serum samples being stored at −20° C. until the time of assay.

3. Immunological Assays i. ELISA With Antipeptide Sera Against env Peptide Coated Plates In this assay, we determined that antiserum raised in an animal by each of peptides 1-6, 31, 64 and 78 of this invention binds to that peptide. Accordingly, the peptides of this invention are immunogenic and elicit a response in test animals.

To carry out the assay, we coated two of four 96-well microtiter plates (Nunc Immuno I) with 50 μl of a mixture of 50 μg/ml uncoupled peptide in PBS (20mM phosphate, 150mM NaCl, pH=7.2) and incubated the plates overnight at room temperature. The third and fourth plates, which served as controls for, respectively, the first and second plates, were treated identically to those plates but were not pre-coated with peptide. We then inverted the plates to empty all wells and washed the plates 3 times with PBS/0.05% Tween-20. The plates were blotted dry by gentle tapping over paper towels. After blotting the plates, we added 350 μl of a 5% fetal calf serum/PBS ("FCS/PBS") solution to each well and incubated the plates for 1 hour at room temperature. We then washed and blotted the plates as before.

We then assayed serum samples pooled from each group of 3 mice on the two pre-coated plates prepared as described above and on two control plates. In the first pre-coated plate, we assayed the antibody response to the immunogen peptide at an initial dilution of 1:10, followed by serial 2-fold dilutions in 5% FCS/PBS. In the second plate, an initial serum dilution of 1:20 was followed by serial 3-fold dilutions in 5% FCS/PBS.

After a 2 hour incubation period, we washed the plates and blotted them dry as described above. We then added 50 μl of 1:2000 dilution of goat anti-mouse-IgG horseradish peroxidase ("HRP") (A.P., heavy and light chain specific, Cappel Laboratories) in 5% FCS/PBS to each well and incubated the plates at room temperature for 1 hour. We then washed the plates with PBS/0.05% Tween-20. We added 42 mM of 3, 3', 5, 5'-tetramethylbenzidine in dimethylsulfoxide ("TMB/DMSO"), 7.35 μl of 30% hydrogen peroxide ("$H_2O_2$") to 50 ml of 0.1M sodium acetate-citric acid buffer (pH=4.92). Subsequently, we added 50 μl of this solution to the wells using a 12 channel multiple pipet. We stopped the enzyme reactions with 50 μl of 2M $H_2SO_4$ when the less dilute samples reached an absorbance of 0.2 O.D. at 650 nm. We then analyzed the plates spectrophotometrically at 410 nm using a microplate reader (Dynatech MR600) and observed that antiserum against each of peptides 1-6, 31, 64 and 78 binds to that peptide.

ii. ELISA With Antipeptide Sera Against Virus-Coated Plates

In this assay, we demonstrated that antisera raised against the peptides of this invention binds to HIV virus-coated plates.

We added 100 μl of carbonate buffer (pH=9.6) containing 5% bovine serum albumin to each well of 96 well microtiter plates coated with authentic HIV virus (a gift of Dr. Robert Gallo) and incubated the plates at room temperature.* Virus-coated microtiter plates are also available from Electronucleonics, Fairfield, N.J. Subsequently, we rinsed the plates 3 times with deionized water. * Due to an inadvertent error, the 873,621 application referred to the preparation of HIV virus-coated plates. The virus-coated plates as employed in the examples of both the '621 application and the present application were a gift of Dr. Robert Gallo. It is our understanding that the plates used were in fact made, or at least could have been made, by coating 96 well microtiter plates (Nunc Immuno I) with 100 μl of a mixture of 5 μg/ml authentic HIV virus in carbonate buffer (pH=9.6), incubating the plates overnight at 4° C., inverting the plates to empty all wells, washing the plates 3 times with deionized water and then blotting them.

After blotting the plates, we added 100 μl of saline-$PO_4$(PBS) containing 20% normal goat serum to each well. We next added 5 μl of human test serum or control serum to each well and incubated the plates overnight at 4° C., or for 2 hours at room temperature. We then washed the pates 3 times with PBS containing 0.05% Tween-20 and blotted them.

We next added 100 μl of a 1:4000 dilution of 1% normal goat serum and goat anti-human-IgG HRP (heavy and light chain specific) in 0.05% PBS-Tween 20 to each well and incubated the plates for 1 hour at room temperature. We had titrated the anti-human-IgG HRP before use to assure a proper final concentration of indicator antibody. At the end of the hour incubation period, we rinsed the plates 2 times with 0.05% PBS-Tween-20 and once with plain PBS. We then added 100 μl of a solution of 0.005% and 0.05% orthophenylene diamine ("OPD")* in Sorenson's phosphate citrate buffer (pH=5) and allowed reaction for 20 minutes at room temperature in the dark. * This is a potential carcinogen which should be detoxified before disposal using a solution of:

50 g $K_2CrO_7$
25 ml 1ON $H_2SO_4$
145 ml $H_2O$

We stopped the reaction by adding 50 μl of 4N $H_2SO_4$ to each well. The plates were read by visual inspection or using a microplate reader at 490 nm.

Each plate had a series of "blank" control wells containing no human serum or anti-human IgG-HRP conjugate and to which one of the following had been added:

saline-$PO_4$(PBS) containing 20% normal goat serum PBS-Tween-20 (0.05%)

Sorenson's phosphate-citrate buffer (pH=5) containing 0.005% $H_2O_2$ and 0.05% OPD.

In addition, each plate had a series of "background" control wells containing no human serum and to which one of the following had been added:

saline-$PO_4$(PBS) containing 20% normal goat serum PBS-Tween-20 (0.05%) containing 1% normal goat serum and goat-anti-human-IgG HRP at a dilution of 1:4000

Sorenson's phosphate-citrate buffer (pH=5) containing 0.005% $H_2O_2$ and 0.05% OPD.

Each test plate also had a negative and positive control serum. We tested antiserum raised against each of peptides 1-6, 31 and 64.

Analysis of the plates revealed that antiserum raised against each of peptides 1, 2, 4 and 31 of this invention binds to the HIV virus.

4. Virus Functional Assays i. Syncytium Inhibition Assay

We assayed the peptides of this invention, as well as antisera raised to them, for their ability to inhibit syncytium formation in a variation of the assay procedure set forth in C. D. Richardson and P. W. Choppin, "Oligopeptides That Specifically Inhibit Membrane Fusion By Paramyxoviruses: Studies On The Site Of Action", Virology, 131, pp. 518-32 (1983). In our assay, we added recombinant HIV env protein, instead of live virus, to cultures of T-4 positive cells in the presence of one of the peptides of this invention, or antiserum raised thereto, and observed the degree of inhibition of syncytium formation and cell fusion in the cultures.

We demonstrated by this assay that the peptides of this invention, as well as antisera raised to them, inhibit virus-mediated events, such as virus adsorption to cells and syncytium formation. In the assay, peptides 1-6, 31 and 64 and antiserum raised against each of peptides 1-6, 31, 64 and 78 were tested. Only peptide 3 inhibited syncytium formation.* Additionally, antiserum raised against each of peptides 1, 2, 4, 5, 31 and 78 inhibited syncytium formation. * Because peptide 64 did not inhibit syncytium formation in this assay and because peptide 64 is identical to peptide 3, the inhibitory activity previously reported for peptide 3 may have been attributable to impurities present with peptide 3 in the sample assayed.

Accordingly, this assay indicates the utility of the peptides of this invention and the antisera raised thereto as therapeutic agents. For example, administration of such peptides to an infected host may inhibit cell-to-cell transmission of the virus and virus-induced cell fusion sufficiently to prevent spread of the infection and ultimate destruction of the immune system. Alternatively, these peptides may be usefully administered in a priming dose which would permit a subsequently infected host to raise neutralizing antibodies effective against the virus.

ii. Virus Neutralization Assay a. HIV Neutralization Based On Lysis Of Cells

We assayed antisera raised to the peptides of this invention, to determine their abilitY to neutralize HIV virus based on lysis of cells. In this assay, we mixed HIV-sensitive cells with the antisera, incubated them for several days and then observed the cells microscopically for lysis.

We observed that antisera to peptides 1, 2, 4, 5 and 31 of this invention neutralized HIV virus, preventing HIV infection and subsequent lysis of cells. Antiserum to each of peptides 6 and 78 did not display such activity and antisera to peptides 3 and 64 were not tested.

Such neutralizing activities indicate that the peptides of this invention and antisera thereto are useful in vaccines for preventing HIV infection. Alternatively, these peptides and antisera are useful in therapeutic compositions for inhibiting virus replication in an infected host.

C. Use Of The Peptides Of This Invention And Their Antibodies In Detecting HIV And Antibodies To HIV Methods and diagnostic kits are presently available which are designed to detect the presence of HIV and antibodies to HIV. Peptides involved in the pathogenicity of HIV infection prepared by the processes of this invention and antibodies raised with them can also be employed in these methods and kits to detect the presence of HIV and antibodies to HIV. These peptides and their antibodies may be packaged in diagnostic kits which allow the rapid and convenient identification of AIDS carriers.

For example, the peptides of this invention or antibodies raised using them can be employed in the immunological diagnostic tests currently available for HIV antigen or antibody detection, e.g., radioimmunoassay or ELISA techniques.

In each assay, both the peptides of this invention and antibodies to these peptides, are used. The antibodies are produced by injecting laboratory animals with the peptides of this invention in a suitable solution, such as Freund's adjuvant, followed by bleeding the animal some six weeks later, removing the red blood cells by centrifugation, and using the resulting serum. Alternatively, monoclonal antibodies to the peptides of this invention may be produced using standard hybridoma techniques.

In one type of radioimmunoassay, antibodies to an HIV peptide produced as above are attached to a solid phase, for example, the inside of a test tube. A sample of the patient's serum is added to the tube, together with a known amount of a peptide of this invention, produced as above, and labelled with a radioactive isotope such as radioactive iodine. Any HIV antigen in the patient's serum will compete with the labelled peptide for binding with the HIV antibodies. The excess liquid is removed, the test tube washed, and the amount of radioactivity measured. A positive result; i.e., that the patient's serum contains HIV antigen, is indicated by a low radioactivity count left in the tube, as compared with a control.

In one type of ELISA test, a microtiter plate is coated with a peptide prepared in accordance with this invention, and to this is added a sample of patient's serum. After a period of incubation permitting interaction of any HIV antibody present in the serum with the HIV antigen, the plate is washed. A preparation of anti-human antibodies, raised in a laboratory animal by injection of semipurified human immunoglobulin, and then linked to an enzyme, is added. Incubation allows an antibody antigen reaction to take place, and the plate is then rewashed. Thereafter, enzyme substrate is added to the microtiter plate and incubated for a period of time to allow the enzyme to react with the substrate. The absorbance of the final preparation is then measured. A large change in absorbance indicates a positive result, i.e., that the patient's serum contains antibodies to HIV.

While we have hereinbefore presented a number of embodiments of this invention, it is apparent that our basic construction can be altered to provide other embodiments which utilize the process of this invention. Therefore, it will be appreciated that the scope of this invention is to be defined by the claims appended hereto rather than the specific embodiments which have been presented hereinbefore by way of example.

We claim:

1. A peptide involved in the pathogenesis of the HIV virus selected from the group consisting of peptides characterized by a sequence of amino acids consisting of the formula: EQIWNNMTWMEWD, NSSSGRMIMEKGEIKNCS, SVEINCTRPNNNTRKSI and D-retro forms thereof.

* * * * *